(12) United States Patent
Birch

(10) Patent No.: US 8,991,436 B2
(45) Date of Patent: Mar. 31, 2015

(54) SYSTEM AND METHOD FOR COVERING AN OPENING OF A FLUID CONDUIT CONNECTOR

(71) Applicant: Evan Tyler Birch, Round Rock, TX (US)

(72) Inventor: Evan Tyler Birch, Round Rock, TX (US)

( * ) Notice: Subject to any disclaimer, the term of this patent is extended or adjusted under 35 U.S.C. 154(b) by 252 days.

(21) Appl. No.: 13/626,328

(22) Filed: Sep. 25, 2012

(65) Prior Publication Data

US 2013/0092274 A1  Apr. 18, 2013

Related U.S. Application Data

(60) Provisional application No. 61/626,284, filed on Sep. 26, 2011.

(51) Int. Cl.
  *B65D 59/00* (2006.01)
  *A61M 39/20* (2006.01)

(52) U.S. Cl.
  CPC .................................. *A61M 39/20* (2013.01)
  USPC ............. 138/96 R; 222/1; 222/187; 222/562; 250/506.1

(58) Field of Classification Search
  CPC .......................... A61M 39/20; A61M 39/165
  USPC ............. 222/553, 562, 563, 1, 187, 182, 420, 222/421; 138/89, 96 R, 89.1–89.4, 92, 96 T; 250/506.1, 515.1, 505.1, 519.1; 215/206, 216, 224, 291, 326
  See application file for complete search history.

(56) References Cited

U.S. PATENT DOCUMENTS

| | | | |
|---|---|---|---|
| 3,307,552 A | 3/1967 | Strawn | |
| 3,450,289 A * | 6/1969 | Esposito, Jr. | 215/214 |
| 3,835,862 A | 9/1974 | Villari | |
| 3,971,955 A * | 7/1976 | Heyer et al. | 250/507.1 |
| 3,987,930 A | 10/1976 | Fuson | |
| 4,846,235 A * | 7/1989 | Handke | 141/311 R |
| 4,936,700 A * | 6/1990 | Morris | 401/196 |
| 7,019,317 B1 * | 3/2006 | Martin et al. | 250/506.1 |
| 7,268,359 B2 * | 9/2007 | Fu et al. | 250/507.1 |
| 7,312,465 B2 * | 12/2007 | Schaber | 250/506.1 |
| 7,419,194 B2 * | 9/2008 | Feith | 220/293 |
| 8,646,488 B1 * | 2/2014 | Shindelar et al. | 138/96 R |
| 2008/0210892 A1 * | 9/2008 | Wagner | 250/515.1 |
| 2012/0067761 A1 * | 3/2012 | Zibouche et al. | 206/524.1 |

* cited by examiner

*Primary Examiner* — Frederick C Nicolas
*Assistant Examiner* — Bob Zadeh
(74) *Attorney, Agent, or Firm* — Meyertons, Hood, Kivlin, Kowert & Goetzel, P.C.; Eric B. Meyertons

(57) ABSTRACT

In some embodiments, a cover device may include a body, a pad, and a grip. The body may include a first opening and at least two arms. The first opening may be in a first end of the body. At least one arm may include a first end and a second end. A first end may be coupled to a wall of the body forming the first opening. At least one arm may extend away from the body further defining and extending the first opening in the body. The pad may be positioned in the first opening in the first end of the body. The pad may absorb, during use, fluids. The body may couple, during use, to a first end of a conduit connector such that the first end is positioned in the first opening such that the first end of the conduit connector is inhibited from contact.

19 Claims, 4 Drawing Sheets

SYSTEM AND METHOD FOR COVERING AN OPENING OF A FLUID CONDUIT CONNECTOR

PRIORITY CLAIM

This application claims priority to U.S. Provisional Patent Application No. 61/626,284 entitled "NUKE CAP" filed on Sep. 26, 2011, which is incorporated by reference herein.

BACKGROUND OF THE INVENTION

1. Field of the Invention

The present disclosure generally relates to enclosing a conduit connector. More particularly, the disclosure generally relates to systems and methods for inhibiting radioactive fluids from exiting a conduit and contaminating adjacent materials.

2. Description of the Relevant Art

Nuclear Medicine is a diagnostic imaging modality which utilizes radioactive tracers to obtain images that demonstrate the function of various organ systems within a patient. These images are obtained by injecting a radiotracer into the patient's bloodstream via a port that is attached to an intravenous catheter. While the location of the port is dependant upon where venous access was achieved, it will usually be located on either the arm or hand. The port is secured using tape or some type of adhesive film and is used repeatedly for intravenous administration of medications throughout the duration of an individual's visit as an inpatient or outpatient. The radioactive tracers used in Nuclear Medicine have to be carefully handled to ensure that any type of radioactive contamination is avoided. Since the radiotracer is a liquid, anything that this liquid comes in contact with becomes radioactive.

In order for the technologist to administer the radiotracer to a patient, the syringe containing the tracer is first screwed onto the port before the plunger is advanced, transferring the syringe contents into the bloodstream. No matter what measures are taken, the face of the port and the distal threads become radioactive due to the interaction with the syringe and syringe contents. Now anything the port comes in contact with also becomes contaminated with radioactivity. Unfortunately, the radiotracer frequently ends up on the patient's gown, shirt, or even their skin. Once images are acquired, the contamination can now potentially become a problem in regard to the diagnostic quality of the study being performed. When a contaminated port comes in contact with the patient's clothing between the injection of the isotope and the beginning of image acquisition, a spot of superficial contamination will be clearly visible in the pictures obtained. If the contamination exists with in the region of interest (organ being imaged), it can compromise the integrity of the nuclear medicine study being performed.

For example, with bone scans, spots of contamination (commonly referred to as hot spots) can be mistaken for metastatic bone lesions or fractures if they are present over the skeleton. In a nuclear stress test, a hot spot visualized over the heart can mask an area of ischemia or possibly impede a physician's ability to interpret tomographic data. With gallbladder studies, it is possible to distort the quantitative data needed when a hot spot exists over the liver/gallbladder. When these situations arise, due to port contamination, the technologist has to take steps to remedy the problem. This usually entails having to replace or move contaminated clothing, scrubbing contaminated skin, and re-imaging the patient. It is also important to note that the Nuclear Regulatory Agency has strict guidelines in place to eliminate the risk of removable radioactive surface contamination, whether it be in the patient's room, in the imaging room, or anywhere for that matter.

Therefore a system and/or method which inhibits a port from inadvertently contaminating surrounding areas with radioactive is highly beneficial.

SUMMARY

This disclosure describes systems and methods for. In some embodiments, a cover device may include a body, a pad, and a grip. The body may include a first opening and at least two arms. The first opening may be in a first end of the body. At least one arm may include a first end and a second end. A first end may be coupled to a wall of the body forming the first opening. At least one arm may extend away from the body further defining and extending the first opening in the body. At least two arms may include a spacing around wall of the body such that second elongated openings are positioned between the at least two arms such that the second end of the at least two arms flex, during use. The pad may be positioned in the first opening in the first end of the body. The pad may absorb, during use, fluids. The body may couple, during use, to a first end of a conduit connector such that the first end is positioned in the first opening such that the first end of the conduit connector is inhibited from contact.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
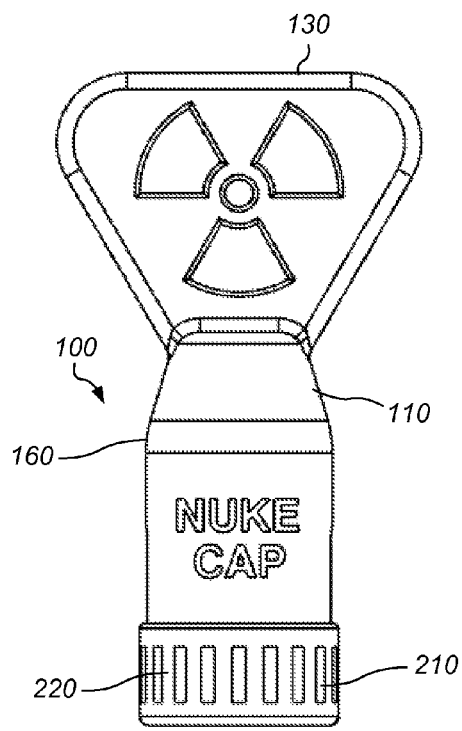
FIG. 1 depicts a diagram of a front view of an embodiment of a cover device.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. §112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

Not only is port contamination an inconvenience, but it costs time and money. The most obvious concern would be compromising a diagnostic procedure, ultimately affecting a subject's quality of care as a patient. What is needed is a way to eliminate radioactive surface contamination due to port contact.

Figure 2:
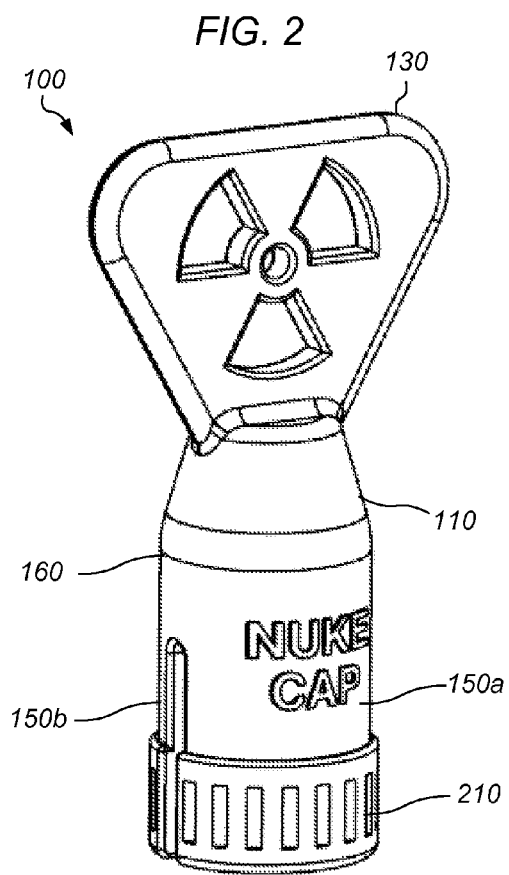
FIG. 2 depicts a diagram of a perspective view of an embodiment of a cover device.
Figure 3:
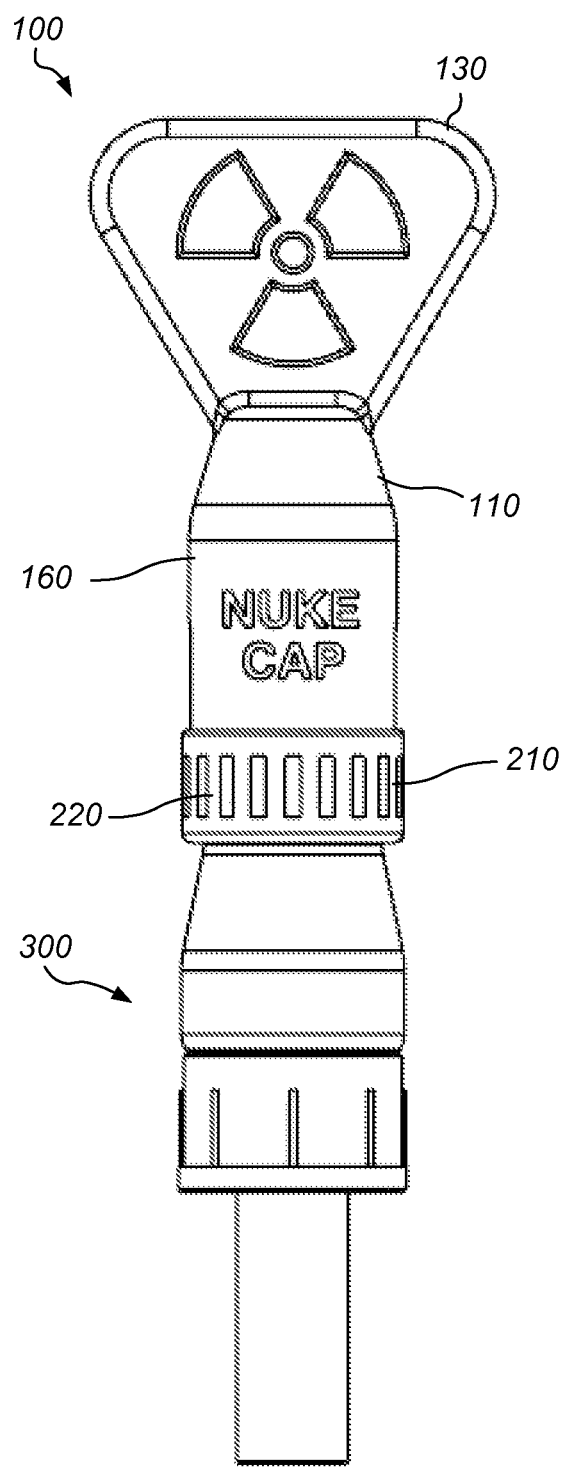
FIG. 3 depicts a diagram of a perspective view of an embodiment of a cover device coupled to a fluid connector.

This disclosure describes systems and methods for inhibiting secondary contamination from radioactive materials due to exposure to a conduit connector (e.g., intravenous port) during use. In some embodiments, a cover device 100 may include a body 110, a pad 120, and a grip 130. Body 110 may include a first opening 140 and at least two arms 150a and 150b. The first opening may be in a first end 160 of the body. FIG. 1 depicts a diagram of a front view of an embodiment of a cover device 100. FIG. 2 depicts a diagram of a perspective view of an embodiment of a cover device 100. FIG. 3 depicts a diagram of a perspective view of an embodiment of a cover device 100 coupled to a fluid connector 300.

In some embodiments, at least one arm 150 may include a first end 170 and a second end 180. First end 170 may be coupled to a wall 190 of body 110 forming first opening 140. At least one arm may extend away from the body further defining and extending the first opening in the body. At least two arms may include a spacing around wall of the body such that second elongated openings 152 (e.g., as depicted in FIG. 4) are positioned between the at least two arms such that the second end of the at least two arms flex, during use.

Figure 4:
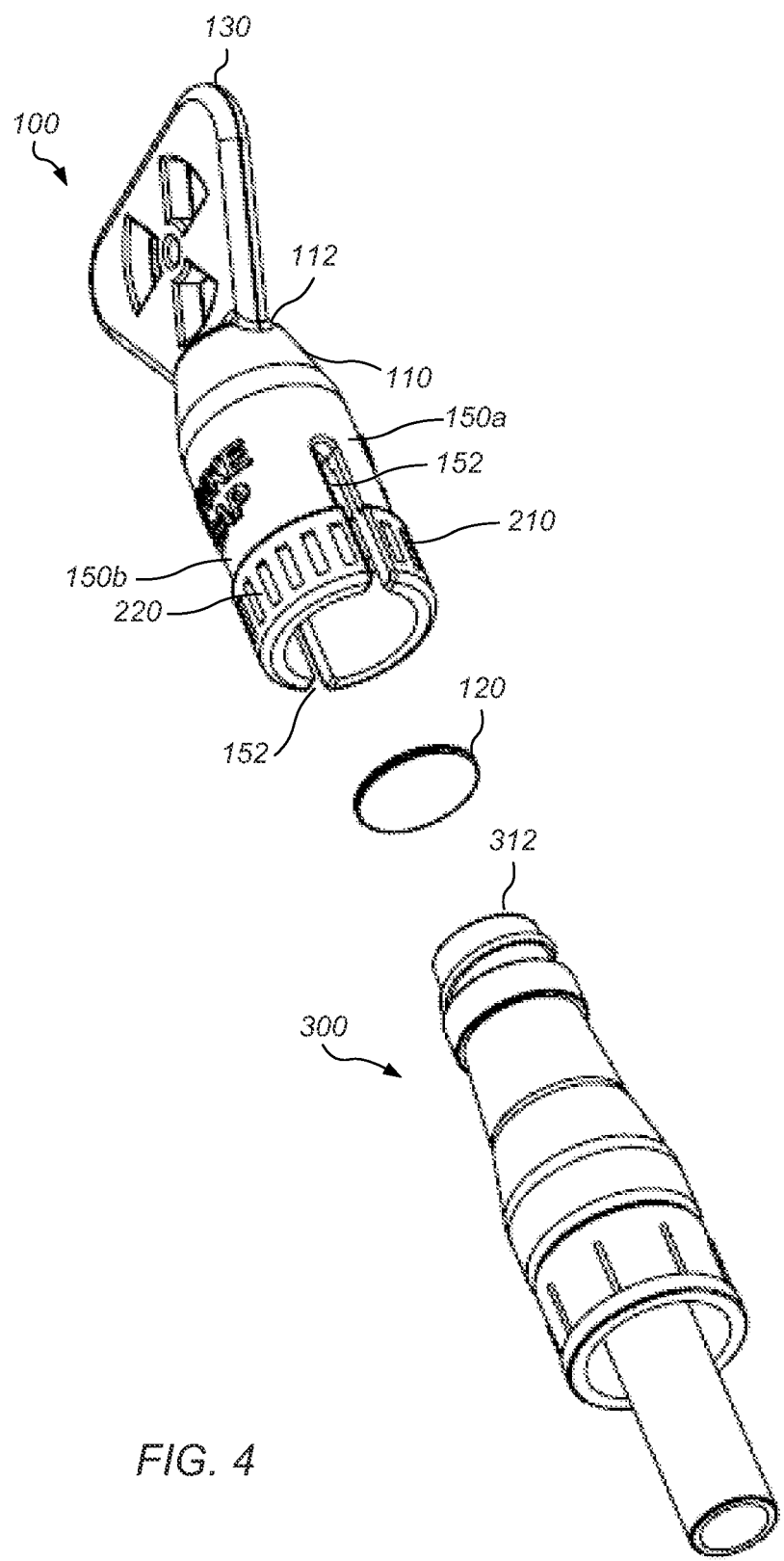
FIG. 4 depicts a diagram of an exploded view of an embodiment of a cover device coupled to a fluid connector.
Figure 5:
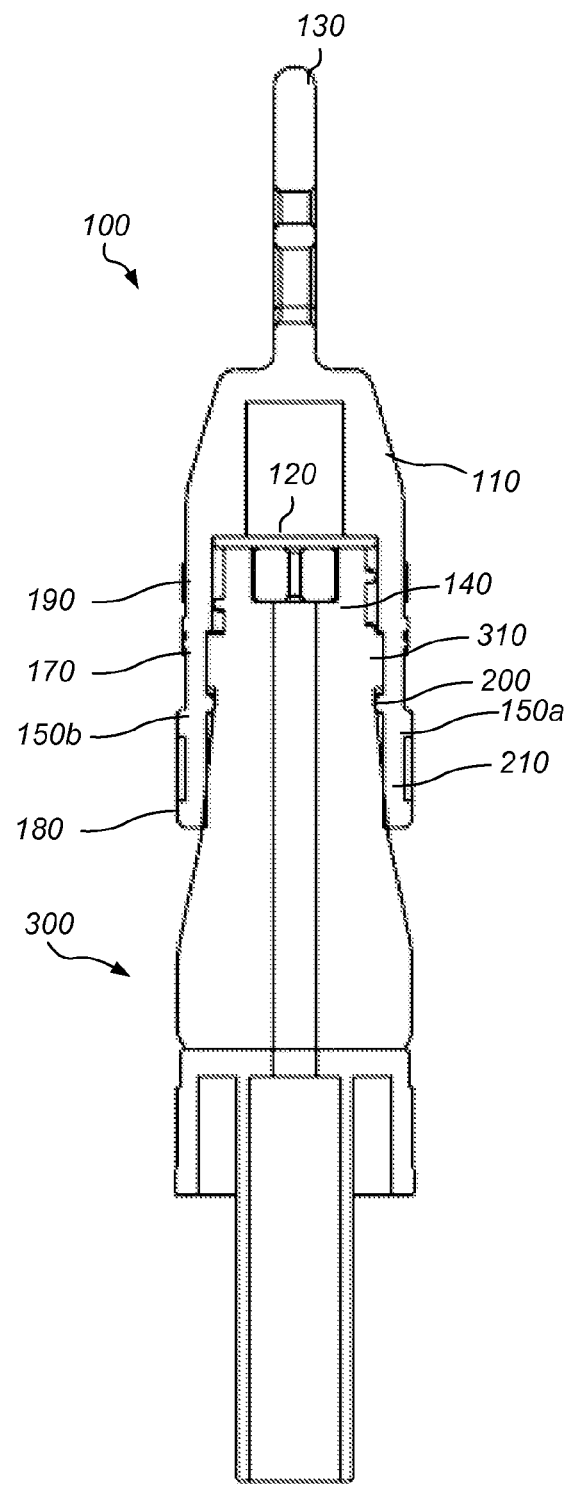
FIG. 5 depicts a diagram of a cross sectional view of an embodiment of a cover device coupled to a fluid connector.

FIG. 4 depicts a diagram of an exploded view of an embodiment of a cover device 100 coupled to a fluid connector 300. FIG. 5 depicts a diagram of a cross sectional view of an embodiment of a cover device 100 coupled to a fluid connector 300. In some embodiments, an arm may include at least one stop 200 positioned on an inner surface of the arm. The stop may inhibit, during use, the disengagement of the body from the first end of the conduit connector. In some embodiments, the cover device may include two arms, each arm including at least one stop positioned on an inner surface of the arm. The arms may be positioned opposite one another. Second openings may be positioned between the lengths of the opposing arms. The openings may allow the arms to flex without interfering with one another.

In some embodiments, stop 200 may include a first raised portion extending out from the inner surface. The raised portion may engage a second raised portion 310 (e.g. threading) extending from an outer surface of the first end of the conduit connector. A force required by a user to engage and/or disengage may be adjusted. The required force may be adjusted by, for example, adjusting the sizes of the raised portions extending from the surfaces. The size of the first and second raised portions may be increased such that that force required to engage/disengage is greater. The required force may be adjusted by, for example, adjusting the shape of the cross section profile of the raised portions extending from the surfaces. For example, a rounded profile (e.g., depicted in FIG. 5) may require less force as opposed to a more angular profile (e.g. square). Different sides of a raised profile may have a different profile such that it may be easier, for example, to engage the cover devise than to disengage the cover device or vice versa.

In some embodiments, the body couples to the first end of the conduit connector using a friction fit.

After a user injects a radiotracer into the conduit connector, the cover device may be removed from its package and placed over the distal end of the conduit connector. The cover device utilizes two arms to encompass the threaded portion of the conduit connector. When pressed down onto the conduit connector, these flexible projections expand allowing the cover device to snap into position. The underside of the finger-like projections contain a ring that snaps over the conduit connector threading, locking the cover device into place. The body of the cover device may be somewhat elongated and extends down to contact the body of the conduit connector for optimal stability and axial alignment.

Pad 120 (e.g., depicted in FIG. 4) may be positioned in first opening 140 in the first end of body 110. The pad may absorb, during use, fluids. The body may couple, during use, to a first end 312 of a conduit connector 300 (e.g., as depicted in FIG. 4) such that the first end is positioned in the first opening and fluid in the conduit connector is inhibited from moving out of the first end. In some embodiments, the pad contacts, during use, the first end of the conduit connector such that the pad absorbs fluids exiting the first end. In some embodiments, the pad may seal an opening in an end of a conduit connector. A pad may be formed from any of a number of absorbent materials. In some embodiments, a pad may be formed from foam rubber.

In some embodiments, the first opening may include, for example, a ridge formed in the surface of the wall of the body which functions to inhibit the pad from falling out or dislodging from the first opening. In some embodiments, the pad may be cut slightly larger than the bottom of the first opening such that the pad forms a friction fit with the first opening inhibiting dislodgement of the pad from the first opening.

The pad may be fixed to the first opening of the cover device, which the face of the port rests against. This pad may remove any residual radiotracer that is left on the conduit connector face. The device may function to inhibit contamination of a surrounding environment by inhibiting contact with an intravenous port.

In some embodiments, at least a portion of an outer surface of at least one of the arms may include a gripping surface 210 which increases, during use, a coefficient of friction between a grasping member (e.g., finger(s)) of a user and the at least one arm. A gripping surface may include any surface which increases a coefficient of friction. A gripping surface may be, in some embodiment, knurled. Knurling may allow hands or fingers to get a better grip on the knurled object than would be provided by the originally smooth surface. The knurled pattern may include a series of straight ridges or a helix of "straight" ridges or a criss-cross pattern. In some embodiments, a gripping surface may include a series of raise ridges 220 (e.g., depicted in FIG. 3).

In some embodiments, grip 130 may include a fingergrip such that a user grasps, during use, the grip to apply pressure to couple or uncouple the body from the first end of the conduit connector. The grip may include a size which facilitates grasping by fingers from and adult human being. A grip may not want to be sized to large such that it does not easily catch or snag on equipment or clothing adjacent the grip.

In some embodiments, cover device 100 may include indicia. Indicia may function to warn users of certain hazards. Indicia may function to instruct users how to use the cover device. In some embodiments, indicia may include radiation warnings. In some embodiments, the grip may include indicia (e.g., as depicted in FIGS. 1-2). Indicia may be printed on the cover device. Indicia may be imprinted, cut, or etched into a surface of the cover device.

In some embodiments, indicia may be cut into a portion of the cover devise such that it extends through the wall of the cover device forming an opening. FIGS. 1-2 depict an embodiment of openings extending through the grip. The openings may have a shape forming a radiation hazard warning. Indicia formed from openings may include advantages, for example, in that the indicia may not be worn away from extended use, smeared or dissolved (especially important in a medical environment where chemical solvents may be present).

The device cover may include a triangular shaped handle with a clearly visible radioactive symbol. The flat triangular handle may lay flat when properly positioned and will allow a user to handle the device cover for placement/removal as needed. The radioactive symbol may be cut out of this grip and will help hospital staff easily identify the presence of radioactivity, so the port can be handled with better care. The center of this radioactive symbol may function as an islet, or point of attachment if necessary. The device cover may be removed and reattached at any point, so a user may have no problem administering meds as the cap snaps back on with ease.

A cover device may be formed from a variety of materials. In some embodiments, a cover device may be formed from inexpensive materials such that the cover devices are designed to be disposable. Once a cover device is used and contaminated (e.g., with radioactive materials), the cover device may be appropriately disposed of. In some embodiments, the cover device may be formed from one or more polymers. The cover device may be formed from molded polyethylene.

In some embodiments, a method of sealing of an end of a fluid connector may include coupling a cover device to a first end of a conduit connector. Coupling the cover device may include positioning the first end of the conduit connector in a first opening of a body of the cover device adjacent a pad positioned in the first opening of the body. Coupling the cover device may include flexing outward away from one another a second end of at least two opposing arms. A first end of the at least two arms may be coupled to a wall of the body forming the first opening at a first end of the body. The at least two arms may extend away from the body further defining and extending the first opening in the body. Coupling the cover device may include engaging an inner surface of a second end of at least two of the arms to an outer surface of the conduit connector.

Once the cover device is placed over the conduit connector and snapped into place, all removable contamination is contained within the cap. Now any chance of inadvertently touching the port to one's clothing or skin is taken out of the equation. The cover device may be individually packaged and sterile. One cap may be intended for one patient.

In some embodiments, the method of sealing of an end of a fluid connector may include inhibiting disengagement of the inner surface of the second end of at least two of the arms to the outer surface of the conduit connector. The method may include absorbing fluids conveyed out of the first end of the conduit connector.

In some embodiments, the method of sealing of an end of a fluid connector may include inhibiting the disengagement of the body from the first end of the conduit connector.

In some embodiments, the method of sealing of an end of a fluid connector may include increasing a coefficient between a grasping member of a user and at least one of the arms using a gripping surface on at least a portion of an outer surface of at least one of the arms.

In some embodiments, the method of sealing of an end of a fluid connector may include grasping a grip 130 coupled to a second end 112 of the body 110 (e.g., as depicted in FIG. 4) using a fingergrip to apply pressure to couple or uncouple the body from the first end of the conduit connector.

In some embodiments, the device cover may remain on the conduit cover until, for example, a Nuclear Medicine procedure is finished. Upon completion of the study, the nuclear tech may remove the cover device and dispose of it in the facility's hot trash. The hot trash is decayed until it has reached background levels of activity before being destroyed.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A cover device, comprising:
   a body, comprising:
      a first opening in a first end of the body;
      at least two arms comprising a first end and a second end, wherein the first end of the at least two arms is coupled to a wall of the body forming the first opening, wherein the at least two arms extend away from the body further defining and extending the first opening in the body, and wherein the at least two arms comprise a spacing around the wall of the body such that second openings are positioned between the at least two arms such that the second end of the at least two arms flex, during use; and
   a pad positionable in the first opening in the first end of the body, wherein the pad absorbs, during use, fluids; and
   a grip coupled to a second end of the body, wherein the grip comprises a fingergrip extending away from the second end of the body such that a user grasps, during use, the fingergrip to apply pressure to couple or uncouple the body from a first end of the conduit connector;
   wherein the body couples, during use, to the first end of the conduit connector such that the first end of the conduit connector is positioned in the first opening such that the first end of the conduit connector is inhibited from contact at least a portion of an outer surface of at least one of the at least two arms comprises a gripping surface which increases, during use, a coefficient of friction between a grasping member of a user and the at least one of the at least two arms.

2. The device of claim 1, wherein fluid in the conduit connector is inhibited from moving out of the first end of the conduit connector by at least the pad.

3. The device of claim 1, wherein the at least two arms further comprise at least one stop positioned on an inner surface of the at least two arms.

4. The device of claim 1, wherein the at least two arms further comprise at least one stop positioned on an inner surface of the at least two arms such that the stop inhibits, during use, disengagement of the body from the first end of the conduit connector.

5. The device of claim 1, wherein the at least one of the at least two arms further comprises at least one stop positioned on an inner surface of the at least one of the at least two arms such that the stop inhibits, during use, disengagement of the body from the first end of the conduit connector.

6. The device of claim 5, wherein at least one of the stops comprises a first raised portion extending out from the inner surface which engages, during use, a second raised portion extending from an outer surface of the first end of the conduit connector.

7. The device of claim 1, wherein the body couples to the first end of the conduit connector using a friction fit.

8. The device of claim 1, wherein the pad contacts, during use, the first end of the conduit connector such that the pad absorbs fluids exiting the first end.

9. The device of claim 1, wherein the grip comprises indicia.

10. The device of claim 1, wherein the grip comprises indicia comprising a radiation warning.

11. The device of claim 1, wherein the grip comprises indicia cut into a surface and/or through the grip.

12. A method of sealing of an end of a fluid connector, comprising:
   coupling a cover device to a first end of a conduit connector, comprising:
      grasping a grip coupled to a second end of a body of the cover device using a fingergrip extending away from the second end of the body to apply pressure to couple or uncouple the body from the first end of the conduit connector;
      positioning the first end of the conduit connector in a first opening of a body of the cover device adjacent a pad positioned in the first opening of the body;
      flexing outward away from one another a second end of at least two opposing arms, wherein a first end of the at least two opposing arms are coupled to a wall of the body forming the first opening at a first end of the body, wherein the at least two opposing arms extend away from the body further defining and extending the first opening in the body;
      engaging an inner surface of the second end of the at least two opposing arms to an outer surface of the conduit connector;
   inhibiting disengagement of the inner surface of the second end of the at least two opposing arms to the outer surface of the conduit connector; and
   absorbing fluids conveyed out of and/or adjacent to the first end of the conduit connector increasing a coefficient between a grasping member of a user and the at least one of the opposing arms using a gripping surface on at least a portion of an outer surface of the at least one of the opposing arms.

13. The method of claim 12, wherein the at least two opposing arms further comprise at least one stop positioned on an inner surface of the at least two opposing arms.

14. The method of claim 13, further comprising inhibiting disengagement of the body from the first end of the conduit connector.

15. The method of claim 13, wherein at least one of the at least one stop comprises a first raised portion extending out from the inner surface which engages, during use, a second raised portion extending from an outer surface of the first end of the conduit connector.

16. The method of claim 12, wherein the body couples to the first end of the conduit connector using a friction fit.

17. The method of claim 12, wherein the grip comprises indicia.

18. The method of claim 12, wherein the grip comprises indicia comprising a radiation warning.

19. The method of claim 12, wherein the grip comprises indicia cut into a surface and/or through the grip.

\* \* \* \* \*